(12) United States Patent
Jensen et al.

(10) Patent No.: US 11,039,999 B2
(45) Date of Patent: Jun. 22, 2021

(54) COMPOSITIONS SUITABLE FOR TREATING CUTANEOUS SIGNS OF AGING

(75) Inventors: Annebeth Siø Jensen, Virum (DK); Annette Strarup Kristensen, Rudersdal (DK); Henrik Enghusen Poulsen, Humlebaek (DK); Jana Vicanova, Prague (CZ); Nico Smit, Amsterdam (NL)

(73) Assignee: Ferrosan APS, Ballerup (DK)

( * ) Notice: Subject to any disclaimer, the term of this patent is extended or adjusted under 35 U.S.C. 154(b) by 3101 days.

(21) Appl. No.: 11/570,680

(22) PCT Filed: Jun. 24, 2005

(86) PCT No.: PCT/DK2005/000427
§ 371 (c)(1),
(2), (4) Date: May 11, 2011

(87) PCT Pub. No.: WO2006/000226
PCT Pub. Date: Jan. 5, 2006

(65) Prior Publication Data
US 2011/0262553 A1 Oct. 27, 2011

Related U.S. Application Data

(60) Provisional application No. 60/582,855, filed on Jun. 25, 2004, provisional application No. 60/609,784, filed on Sep. 14, 2004.

(30) Foreign Application Priority Data

Jun. 25, 2004 (DK) .............................. PA200400995
Sep. 14, 2004 (DK) .............................. PA200401397

(51) Int. Cl.
| | | |
|---|---|---|
| *A61K 36/00* | (2006.01) | |
| *A61K 8/67* | (2006.01) | |
| *A61K 8/73* | (2006.01) | |
| *A61K 8/27* | (2006.01) | |
| *A61Q 19/08* | (2006.01) | |
| *A23L 33/15* | (2016.01) | |
| *A23L 33/105* | (2016.01) | |
| *A61K 8/9789* | (2017.01) | |

(52) U.S. Cl.
CPC ............ *A61K 8/676* (2013.01); *A23L 33/105* (2016.08); *A23L 33/15* (2016.08); *A61K 8/27* (2013.01); *A61K 8/678* (2013.01); *A61K 8/735* (2013.01); *A61K 8/9789* (2017.08); *A61Q 19/08* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,299,925 B1 | 10/2001 | Xiong et al. | |
| 6,682,732 B1 * | 1/2004 | Blake et al. ................. | 424/94.4 |
| 2002/0012714 A1 * | 1/2002 | Olson ...................... | A61K 8/02 |
| | | | 424/766 |
| 2003/0059501 A1 * | 3/2003 | Rivier .......................... | 426/103 |
| 2004/0023894 A1 | 2/2004 | Hasler-Nbuyen et al. | |
| 2004/0161435 A1 * | 8/2004 | Gupta ......................... | 424/401 |
| 2004/0175351 A1 | 9/2004 | Liu et al. | |
| 2005/0084546 A1 | 4/2005 | Smith et al. | |
| 2005/0154066 A1 * | 7/2005 | Fujii ....................... | A61K 8/347 |
| | | | 514/690 |
| 2005/0281869 A1 * | 12/2005 | Kruse et al. ................ | 424/449 |

FOREIGN PATENT DOCUMENTS

| | | |
|---|---|---|
| JP | 2264720 A | 10/1990 |
| JP | 4164031 A | 6/1992 |
| JP | 2003192528 A | 7/2003 |
| JP | 2003226613 A * | 8/2003 |
| JP | 2003226613 A * | 8/2003 |
| JP | 2003532680 A | 11/2003 |
| WO | WO 01/26486 A1 | 4/2001 |
| WO | WO-01/78674 A1 | 10/2001 |
| WO | WO-0185182 A2 | 11/2001 |
| WO | WO 02/39973 A1 | 5/2002 |
| WO | WO 03/075861 A1 | 9/2003 |
| WO | WO 03/086329 A1 | 10/2003 |

OTHER PUBLICATIONS

Fragrance Journal, 1990, vol. 18, No. 11, pp. 8-12.

\* cited by examiner

*Primary Examiner* — Qiuwen Mi
(74) *Attorney, Agent, or Firm* — Roshni A. Sitapara

(57) ABSTRACT

Compositions comprising vitamin E, vitamin C, and white tea extract for treating cutaneous signs of aging are disclosed. The compositions reduce signs of wrinkles and improve other skin conditions, such as increased skin elasticity and skin softness. Moreover, the prevention or treatment of unhealthy skin, such as aged skin or skin overexposed to sunlight, may advantageously be accomplished by the administration of the compositions of the present invention The compositions includes the combination of a number of different components, which interact to provide the desired improvements to the skin Further advantageous ingredients of the compositions may comprise, naturally occurring antioxidants extracted from e g grape seeds and tomato, an extract comprising glycosaminoglycans, a transition metal component in an amount effective to bind collagen and elastic fibers and thicken skin, and a catechin-based component present in an amount sufficient to inhibit the presence of anti-collagen enzyme in the skin.

17 Claims, 3 Drawing Sheets

COMPOSITIONS SUITABLE FOR TREATING CUTANEOUS SIGNS OF AGING

BACKGROUND OF THE INVENTION

The present invention relates to compositions comprising vitamin E, vitamin C, and white tea extract for treating preventively and/or curatively, cutaneous signs of aging. In a preferred embodiment the invention relates to the use of vitamin E, vitamin C, and white tea extract or compositions comprised thereof to reduce cutaneous signs of aging by enhancing the release of G1-arrested cells, whereby cells recover more rapidly.

Human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by the structural changes in the skin due to aging and excessive sun exposure. The physiological changes associated with skin aging include impairment of the barrier function and decreased turnover of epidermal cells, for example. [Cerimele, D., et al., Br. J. Dermatol., 122 Suppl. 35, p. 13-20 (April 1990)].

The mechanical properties of the skin, such as elasticity, are controlled by the density and geometry of the network of collagen and elastic fiber tissue therein. Damaged collagen and elastin lose their contractile properties, resulting in skin wrinkling and skin surface roughness. As the skin ages or becomes unhealthy, it acquires sags, stretch marks, bumps, bruises or wrinkles, it roughens, and it has reduced ability to synthesize Vitamin D. Aged skin also becomes thinner and has a flattened dermoepidermal interface because of the alterations in collagen, elastin, and glycosaminoglycans. [Fenske, N. A., and Lober, C. W., J. Am. Acad. Dermatol., 15:571-585 (October 1986); Montagna, W. and Carlisle, K., Journal of Investigative Dermatol., 73(1):47-53 (1979)].

A variety of vitamins and minerals have in individuals been administered to treat certain skin and other problems that occur when the patient has a deficiency of that vitamin or mineral. Vitamin A, for example, assists in the treatment of acne and to facilitate wound healing; vitamin C (ascorbic acid) assists in the prevention of skin bruising and wound healing; vitamin E is an antioxidant; and copper assists in the treatment of elastic tissue defects. [Neldner, K. H., Amer. Acad. Derm. Anni. Mtg., Wash D.C., Dec. 6, 1993]. Topical use of vitamin C is also believed to ward off sun damage, reduce breakdown of connective tissues, and possibly promote collagen synthesis. [Dial, W., Medical World News, p. 12, March 1991]. Vitamin E is used topically as an anti-inflammatory agent, for enhancement of skin moisturization, for UV-ray protection of cells, and for retardation of premature skin aging.

Catechin-based preparations, including proanthanols and proanthocyanidins are powerful naturally occurring antioxidants. These compounds are found in flowers, plant leaves, and grape seeds, for example. [Lubell, A, Cosmetic Dermatol. 9(7): 58 & 60 (July 1996)]. The potential importance of nutrition to the aging process has been a topic of interest for many decades and has encompassed not only the effect of diet on cell senescence and death but also the role nutrients play in delaying the decline in immuno-competence, skeletal integrity, hormonal balance, and other bodily functions often associated with aging organisms. Several nutrients, including vitamins and essential minerals, have been linked beneficially with these disorders.

Aging is associated with changes in physical characteristics and a decline of many physiological functions in humans. Although the phenomenon of aging is well known, the basic nature of aging is not well understood. Among the several theories of aging, the free radical theory of aging, first proposed in 1956 by Harman (J. Gerontol. 1956, 11, 198-300) has received increasing attention in the last decades. The theory postulates that the free radical reaction is a single common process that might be responsible for aging and intimately involved in many age-associated disorders. The modern concept of this theory is supported by accumulated data in recent years elucidating the time-dependent shift in the antioxidant/prooxidant balance in favor of oxidative stress that may lead to dysregulation of cellular function and aging.

A complex intrinsic antioxidant defense mechanism present in most aerobic organisms scavenges free radicals and reduces oxidative stress. Free radicals and oxidative stress will lead to cytotoxicity and contribute to the aging process. A strong positive correlation between maximum life span and potential antioxidant capacity has been determined in several oxidative defense mechanisms (Cutler, R. G., 1991, Am. J. Clin. Nutr., 53, 373S-379S). Moreover, a positive correlation between tissue concentrations of specific antioxidants and the inherent life span in mammals has been elucidated.

Antioxidant activity is provided by naturally occurring substances including vitamin C, vitamin E, glutathione, beta-carotene, and histadine. Furthermore, intracellular enzymes such as superoxide dismutase, glutathione peroxidase, thioredoxin reductase, and catalase also provide protection against activated oxygen radicals. The different clinical patterns of photoaging are well known and have been well described in the literature. Major age-related cutaneous changes include dryness, wrinkling, laxity and development of various benign neoplasms. The end result of both intrinsic aging and chronic exposure to ultraviolet light and other potential exogenous hazards is a skin that is wrinkled, yellow, lax, dry, and leathery. Furthermore, precancerous as well as cancerous lesions develop as consequences of repeated solar radiation.

The antioxidant vitamins E and C and -carotene have received considerable attention for their potential role in the prevention of degenerative diseases such as cancer and cardiovascular disease.

It is known that vitamin C acts as an antioxidant and free radical scavenger that reacts directly with super oxide, hydroxyl radicals, and singlet oxygen produced during normal cellular metabolism. Oxygen is necessary for life. Oxygen also comes in several radical forms that have been implicated in both initiation and post-initiation stages of the carcinogenic process as well as in invasion and metastatic processes.

Aside from its antioxidant properties, there is no single universal accepted and proven explanation for vitamin C's cancer fighting properties. It is likely that a variety of pathways are involved, which include (1) fortifying the immune system by increased lymphocyte production; (2) salvaging cellular free radical damage; (3) inhibition of hyaluronidase, keeping the ground substance around the tumor intact and preventing metastasis; (4) killing oncogenic viruses through its enhancement of phagocytic activities; (5) correction of an ascorbate deficiency commonly seen in cancer patients; (6) stimulating collagen formation and its stabilization necessary for "walling off" tumors; and (7) neutralization of carcinogenic toxins.

As a key nutrient required for strong immune response and an important fat-soluble antioxidant, vitamin E's preventive role in cancer has been well proven. With cancer in remission, the use of vitamin E as a preventive nutritional agent to prevent further oxidative stress is a cornerstone of any cancer remission nutritional protocol.

U.S. Pat. No. 5,648,377 describes formulations and combinations of lipophilic and hydrophilic antioxidants and the use thereof in the therapeutic, foodstuff, dietic, and cosmetic fields. These formulations are based on the use of carotenoids, procarotenoids and derivatives thereof with polyphenols of catechic structures. These formulations can be used in the prevention of physiopatological conditions related at least partially to an over-production of free radicals, particularly aging, artherosclerosis and cancer. Accordingly it was surprisingly observed that the combination of hydrophilic antioxidant with a lipophilic one exerts an antioxidant action far greater than that of the sum of the single compounds tested at equal concentrations. The specifically disclosed antioxidants or sources thereof are a procyanidol oligomer extracted from *Vitis vinifera*, lycopene, vitamin E and procyanidin A2.

U.S. Pat. No. 5,156,852 discloses a composition for scavenging free radicals and other oxidants associated with eye diseases comprising vitamins E and C, zinc acetate, copper, selenium, manganese, and at least one of L-cysteine, pyridoxine, and riboflavin. The vitamins C and E serve as antioxidants, while the zinc acetate, copper, selenium and manganese serve as cofactors for metalloenzymes with scavenge oxidizers. The remaining three compounds tend to enhance gluthathion concentration.

Antioxidants are important elements in the body's defense against oxidative stress and are known to have a general anti-aging property as well as a specific disease-protective function. In this respect important antioxidants are e.g. vitamin E, vitamin C and carotenes, which in combination offers synergistic cell protection (Boehm, F., Edge, R., McGarvey, D J, FESS Lett. 436, 387-389, 1998). Furthermore other antioxidants without vitamin functions originating from food, such as flavonoids, polyphenols, or lycopene have very important antioxidative functions.

Certain vitamins and minerals, antioxidants, and plant extracts are generally known to have beneficial health effects. For example, several beneficial aspects of antioxidants have been known for many years. Antioxidants are chemicals that react with free radicals, such as hydroxy radical, to protect certain biological systems. The removal of free radicals from the body has been suggested to increase human longevity; specifically, the presence of antioxidants including carotenoids, vitamin E, and uric acid is suggested to have a positive correlation with
resistance to spontaneous autooxidation of tissues and oxidative damage to DNA in mammals (Cutler, R., Am. J. Clin. Nutr. 53: 373S-9S (1991)). Antioxidants are also known to limit destruction of healing brain tissue by free radicals as shown by the method for resuscitating the brain using vitamins such as A, E and C and selenium (U.S. Pat. No. 5,149,321).

In addition to their antioxidant activity, vitamins A, C, and E are well known to have other beneficial health effects. For example, vitamin E is known to help maintain proper blood sugar levels. As another example, vitamin C is known to play an integral role in the integrity of connective and structural tissues in the body. Vitamin A is known to play a role in the good vision as well as in growth and development. Hence, an adequate supply of these vitamins is essential in maintaining optimum health. The use of vitamins A, E, C and selenium has been proposed as a means to inhibit or prevent collagen cross-linking in human skin when used in combination with certain active peptides 0/VO 90/06102).

U.S. Pat. No. 5,648,377 relates to the combination of lycopene with an extract of *Vitis vinifera* (grape seed extract) demonstrating a synergistic antioxidant action. U.S. Pat. No. 6,627,231 teaches the surprising discovery that the administration of the combination of grape seed extract, lycopene, vitamin C, vitamin E, and 13-carotene significantly increases, in a synergistic manner, the cell protection. According to this disclosure the cell protection with the mentioned substances is statistically greater than the combination of grape seed extract and lycopene or vitamin E and lycopene.

WO 01/78674 discloses compositions useful in the treatment of skin ageing in form of inter alia capsules and tablets. These compositions include the active principles lycopene, grape seed extract, vitamin C and vitamin E.

WO 99/48386 discloses a food supplement, which includes pycnogenol, lycopene, vitamin C, and vitamin E.

U.S. Pat. No. 5,895,652 relates to an oral supplementation program to maximize the body's inherent biochemical pathways to thereby limit damage otherwise caused by deficiencies during the normal aging process. The individual components of this supplement are given in a very long list, which extends over several pages, and include lycopene, vitamin C, vitamin E, and grape seed extract.

WO 98/33494 discloses nutrient and therapeutic compositions useful against vascular and capillary disorders and also combines different antioxidants or components having antioxidant effect including lycopene, grape seed extract, vitamin C, vitamin E and tea polyphenols.

WO 01/51088 discloses compositions for reducing the risk of cardiovascular diseases and includes lycopene, vitamin E, vitamin C, and grape seed extract.

WO 02/071874 discloses a composition intended to prevent or restore age-related functional deficits in mammals and comprises vitamin C, vitamin E, lycopene, chamomile dry extract, grape seed extract, and tea catechins.

Thus the prior art teaches the combined action of at least vitamin C, vitamin E, lycopene and grape seed extract, for reducing oxidative damage to cells and thereby prevent various symptoms associated with aging.

The main role of antioxidants is to protect cells from oxidation by reactive oxygen species (ROS) or other free radicals. ROS are highly active intermediates, which carry an unpaired electron and readily interact with other molecules in human tissue, resulting in an oxidative reaction. ROS are produced as a normal byproduct of mitochondrial respiration and are essential for normal cell function. However, ROS can also result from oxidative stress, induced by exogenous factors and have been associated with a number of disease processes. Normally, antioxidants found in the body scavenge these nonessential ROS and transform them into stable compounds through electron transfer. This action of antioxidants prevents oxidative damage by ROS to cellular components. However, when oxidative stress is excessive, the body's antioxidants can be depleted, resulting cell damage. Excessive oxidative stress can be induced by some antineoplastic agents (which generate ROS) as well as by the cancer itself. Because of this, research has been conducted to determine the effects of antioxidants on cancer cells and on the actions of antineoplastic agents.

During periods of oxidative stress, excess ROS results in a higher production of lipid peroxidase. Lipid peroxidase subsequently affects the cell cycle either by prolonging the G1 phase or having cells enter the GO phase.

In proliferating cells, the cell cycle consists of four phases. Gap 1 (G1) is the interval between mitosis and DNA replication that is characterized by cell growth. The transition that occurs at the restriction point (R) in G1 commits the cell to the proliferative cycle. Replication of DNA occurs during the synthesis (S) phase, which is followed by a second gap phase (G2) during which growth and preparation for cell division occurs. Mitosis and the production of two daughter cells occur in M phase.

Passage through the four phases of the cell cycle is regulated by a family of cyclins that act as regulatory subunits for cyclin-dependent kinases (cdks). The activity of the various cyclin/cdk complexes that regulate the progression through G1-S-G2 phases of the cell cycle is controlled by the synthesis of the appropriate cyclins during a specific phase of the cell cycle. The cyclin/cdk complex is then activated by the sequential phosphorylation and dephosphorylation of the key residues of the complex, located principally on the cdk subunits.

The cyclin cdk complex of early G1 is either cdk2, cdk4, or cdk6 bound to a cyclin D isoform. There are several proteins that can inhibit the cell cycle in G1. If DNA damage has occurred, p53 accumulates in the cell and induces the p21-mediated inhibition of cyclin D/cdk. Mdm2, by facilitating the nuclear export/inactivation of p53, becomes part of an inhibitory feedback loop that inactivates p21-mediated G1 arrest. Similarly, activation of TGF-b receptors induces the inhibition of cyclin D/cdk by p15, while cyclic AMP inhibits the cyclin D/cdk complex via p27. If the cyclin D/cdk complex is inhibited, retinoblastoma protein (Rb) is in a state of low phosphorylation and is tightly bound to the transcription factor E2F, inhibiting its activity.

Passage through the restriction point and transition to S phase is triggered by the activation of the cyclin D/cdk complex, which phosphorylates Rb. Phosphorylated Rb dissociates from E2F, which is then free to initiate DNA replication. Cyclin E/cdk2 accumulates during late G phase and triggers the passage into S phase. The entire genome is replicated during S phase. The synthesis and accumulation of cyclin B/cdc2 also begins during S phase, but the complex is phosphorylated at $Thr^{14}$-$Tyr^{15}$ and is inactive. Cyclin A/cdk2 accumulates during S phase and its activation triggers the transition to G2, a phase characterized by the accumulation of cyclin B/cdc2, the inhibition of DNA replication, cell growth and new protein synthesis.

Summarized each cell is equipped with a very sophisticated mechanism to repair DNA damage before new synthesis of DNA (in S-phase) and cell division during mitosis (M-phase). As a reaction to DNA damage certain cell cycle regulators such as p16 and p53 are increased which results in the inhibition of cell cycle progression via inhibition of specific cyclin dependent kinases (cdk 4 and cdk2). This enables the cell to repair the DNA damage before new synthesis of DNA starts at the so-called G1/S checkpoint preventing cells to move from G1 into S-phase (FIG. 1). p53 is increased in skin after UV induced damage as was shown in skin biopsies and the recovery to basic levels is a measure of repair status of the skin. p16 is elevated at the stage of cell senescence.

In earlier work (Emri et al, J Invest Dermatol 115: 435-440, 2000) a dose dependent increase of fibroblasts was found in G2/M, 4 days after UV irradiation.

The release of G1-arrested cells to the S phase depends on the degree of damage to the DNA. Since the degree of DNA damage is directly linked to the oxidative level of the cells, it would be expected that the most efficient reduction of the oxidative level in turn would give rise to the most rapid release of G1-arrested cells into the S phase. Judged from the prior art this would imply the combined action of at least vitamin C, vitamin E, lycopene and grape seed extract.

Abid-Essefi et al (TOXICOLOGY, 192 (2-3): 237-248 Nov. 5 2003) describe that Vitamin E may act by maintaining prolonged cell cycle arrest during which time DNA repair takes place.

Galli et al (ARCHIVES OF BIOCHEMISTRY AND BIOPHYSICS, 423 (1): 97-102 Mar. 1 2004) describe that vitamin E exerts an inhibitory effect on cyclin D1 expression parallel to the retardation of cell growth.

Gysin et al (FASEB JOURNAL, 16 (12), October 2002) describe that vitamin E inhibits cell cycle progression via reduction of cyclin D1 and cyclin E levels.

Panaro et al (British Journal of Cancer (1999) 80, 1905-1911) showed that the cell cycle was blocked by various antioxidants, including vitamin C and numerous flavonoids.

Hence, the prior art suggest that administration of antioxidants results in an extension of the cell cycle block.

UV (UVB and UVA) radiation has shown to cause various types of damage in skin. UVB radiation (wavelengths 280-315 nm) continuously induces (DNA) damage in the upper layer of our skin, the epidermis. UVA radiation (315-400 nm) reaches deeper into the lower skin layer, the dermis but fortunately this type of radiation is much less damaging than the high energetic UVB radiation.

DNA damage is probably the most serious damage that can be caused by UV radiation since it directly affects the genetic potential of a cell. UVB induced DNA damage leads to the induction of cell cycle regulators with subsequent cell cycle arrest during which time DNA repair can take place. UVA irradiation of cells may cause damage to the DNA via indirect mechanisms including the formation of oxygen radicals. So far it has not been fully clarified how UVA induced damage affects cell cycle control and whether prevention of oxidative damage will positively influence cell cycle progression.

Surprisingly the applicant has discovered that the combined action of vitamin C and vitamin E, preferably in conjunction with white tea extract, gives rise to a fast release of cells from G1-arrest.

This shows that the oxidative level of the cells and the associated DNA damage cannot be directly correlated with the time needed for the cells to regenerate and enter the S phase. An effective regimen for treating cutaneous signs of aging will certainly depend on the ability of cells to continue growing after oxidative damage has taken place.

BRIEF DESCRIPTION OF THE INVENTION

Figure 1:
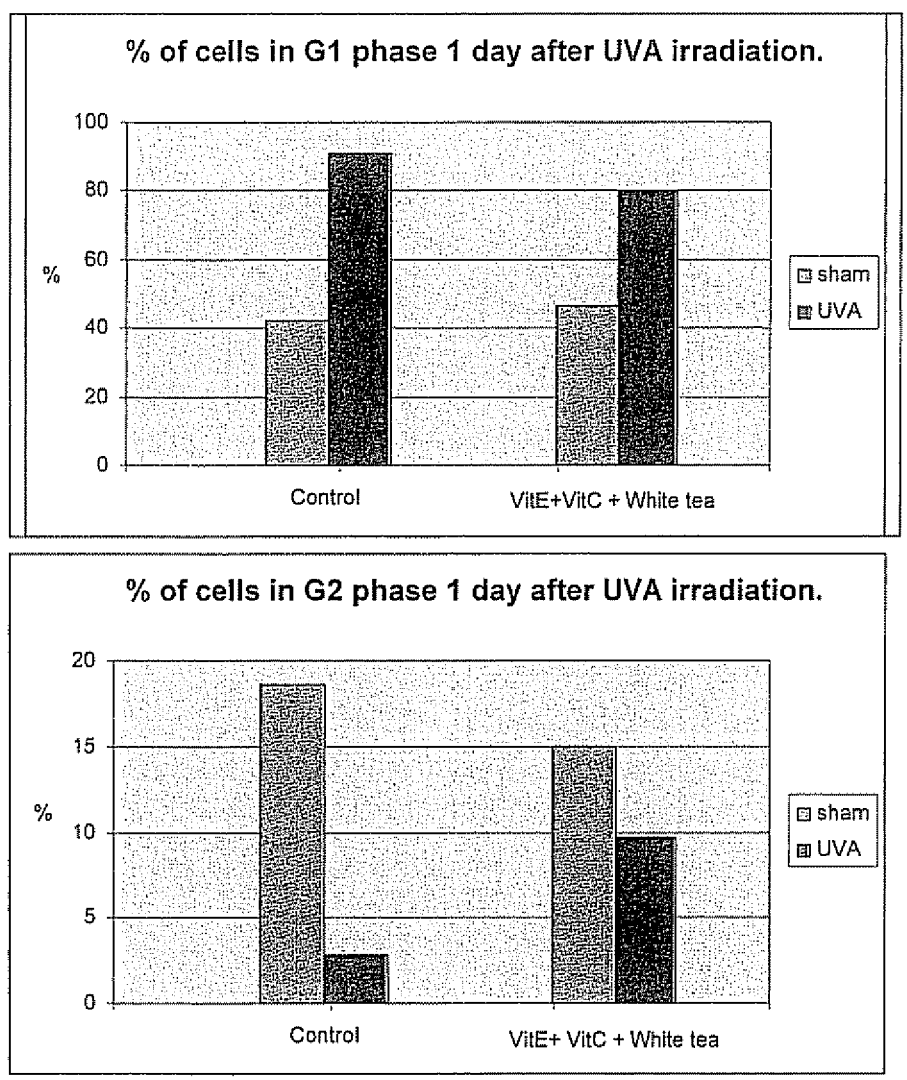
FIG. 1 illustrates the distribution of cells in G1 and G2 phase one day after UVA irradiation (dark) compared to sham irradiated fibroblast cultures (grey)

One aspect of the invention is directed to an orally administered composition comprising vitamin E, vitamin C, and white tea extract for treating either preventively or curatively individuals suffering from cutaneous signs of aging. In particular the signs of aging are reduced when the composition acts on fibroblasts.

According to the present invention the potential benefits of an oral nutraceutical supplement containing vitamin C, E, and white tea extract along with different plant extracts, glycosamines and minerals, in reversing certain clinical features of cutaneous aging (e.g. wrinkles) are achieved. By definition, nutraceuticals are substances that have health benefits, including the prevention and treatment of diseases.

The role of several minerals in cellular protection from both intrinsic and extrinsic factors has previously been documented. Selenium, silicium, copper, zinc and manganese are the minerals that may be included in formulations according to the present invention. Zinc acts as a cofactor with superoxide dismutase (SOD), which in turn acts in concert with copper SOD, mitochondrial manganese SOD, glutathione peroxidase and catalase as essential cellular antioxidants. Manganese, a transition metal, binds collagen fibers and inhibits the elastase enzyme, which breaks down both collagen and elastic tissue. Manganese also plays a key role in the synthesis of collagen and glycoproteins, and acts as a cofactor for catalyzing the conversion of the glucosamine into hyaluronic acid. In addition, manganese has been shown to protect cultured human skin fibroblasts against oxidative injury by UVA and hydrogen peroxide.

The composition may comprise further ingredients, which are known to inhibit the process of aging. In particular plant extracts such as white tea extract, grape seed extract, tomato extract with high content of lycopene, soy extract, borage oil, flaxseed oil, chamomile dry extract and special fractionated coconut oil are suitable in connection with the present invention. Moreover ingredients such as those contained in extracts from various tissues, including cartilage, may be included in the composition.

The compositions of the invention can be formulated in any form whatever suited. Preferably the compositions of the invention are formulated for oral administration. For oral administration the compositions of the invention can be provided in any suitable form, particularly in the form of a solution to be taken orally, of a tablet, of a capsule, of a nutritional food or of a nutritional supplement. Such compositions additionally comprise at least one appropriate excipient and/or co-adjuvant suited for oral administration.

Preferred Embodiments

A formulation for the reduction of wrinkles and the improvement of other skin conditions, such as increased skin elasticity and skin softness, has now been discovered. Moreover, the prevention or treatment of unhealthy skin, such as aged skin or skin overexposed to sunlight, may advantageously be accomplished by the administration of the composition of the present invention to a human in need of treatment. The composition includes the combination of a number of different components, which interact to provide the desired improvements to the skin.

The advantageous pharmaceutical composition of the present invention prevents and improves skin conditions by using Vitamin E and vitamin C in amounts sufficient for skin cells to escape G1-arrest. Further advantageous ingredients of the composition may comprise, naturally occurring antioxidants extracted from e.g. grape seeds and tomato, an extract comprising glycosaminoglycans, a transition metal component in an amount effective to bind collagen and elastic fibers and thicken skin, and a catechin-based component present in an amount sufficient to inhibit the presence of anti-collagen enzyme in the skin.

A thicker dermis desirably reduces the wrinkling and lines that occur when areas of the skin become thin. In addition to the surprising effect of deblocking the cell cycle, antioxidants, such as vitamin C, inhibit collagenase and elastase, enzymes that break down collagen and elastic tissues. These antioxidants assist in the prevention of additional wrinkles and facilitate the healing of skin tissues. Finally, transition metal components are included to bind collagen fibers and inhibit elastase, an enzyme that also breaks down collagen and elastic tissue.

The composition includes a primary antioxidant, which typically is a vitamin C source and preferably is ascorbic acid, or a pharmaceutically acceptable salt or ester thereof, and more preferably is ascorbyl palmitate, dipalmitate L-ascorbate, sodium L-ascorbate-2-sulfate, or an ascorbic salt, such as sodium, potassium, or calcium ascorbate, or mixtures thereof. When oral formulations of the composition are used, it is preferred that a non-acidic form of vitamin C be used to reduce the stomach irritation that may occur when using an acidic form.

The term "extract comprising glycosamines" is intended to include cartilage, components that may be extracted therefrom, and derivatives thereof, including synthetic forms of compounds extractable from cartilage and synthetically prepared derivatives. Such compounds may alsobe found in other tissue containing connective tissue, e.g. skin, and may be extracted therefrom. The cartilage may be selected from the group consisting of marine animal cartilage, fish cartilage, mollusc cartilage and land-dwelling mammal cartilage, Marine animals may be selected from the group consisting of a whale, dolphin and seal; the fish may be selected from the group consisting of shark, salmon, tuna, cod and other known fish; the mollusc may be a squid; and land-dwelling animals may be selected from the group consisting of a bovine, porcine, chicken, duck and turkey.

The cartilage or extracts therefrom are preferably selected from bovine cartilage, porcine cartilage, shark cartilage, squid cartilage, chicken cartilage and salmon cartilage. Cartilage itself may be used. It may typically be used in the form of dried, e.g. lyophilised, comminuted cartilage. Useful extracts of the above mentioned types of cartilage or other tissue containing the appropriate components may typically be prepared through partial enzymatic proteolytic hydrolysis of cooked tissue followed by filtration and drying of the hydrolysate, e.g. through spray drying or lyophilisation. The cartilage extract typically comprises of one or more compounds extractable from cartilage, and preferably comprises glycosaminoglycans, optionally bound to a peptide.

The cartilage extract preferably comprises chondroitin sulphate, keratan sulphate, hyaluronic acid, or dermatan sulphate or mixtures thereof. The term cartilage extract is intended to include compounds obtainable from cartilage but the compounds may actually be obtained from other sources.

The term cartilage extract may relate to compounds extractable from cartilage or derivatives thereof. As stated, the cartilage extract may come from other natural sources but may be from a synthetic source, i.e. synthetically or semi-synthetically prepared.

The cartilage extract preferably comprises glycosaminoglycans selected from the group consisting of a chondroitin ester, a keratan ester, hyaluronic acid or an ester thereof, a dermatan ester, heparin, and a heparan ester. These may be bound to a protein or peptide or as epimeric or polymeric forms of chondroitin ester, a keratan ester, hyaluronic acid or an ester thereof, a dermatan ester, heparin, a heparan ester, preferably chondroitin sulphate, keratan sulphate, hyaluronic acid or an ester thereof, a dermatan sulphate, a heparin, a heparan sulphate The glycosaminoglycans may be selected from the group consisting of chondroitin sulphate and keratan sulphate, each of which may be optionally bound to a peptide. Most preferably, the composition of the present invention comprises 5% cartilage extract comprising chondroitin sulphate, optionally bound to a peptide.

In a preferred embodiment, the composition of the present invention comprises less than 1% weight/weight collagen, preferably less than 0.5%, particularly preferably less than 0.1% collagen protein. In the typical manner collagen extract is prepared, it does not comprise collagen to any appreciable amount. The extract is preferably prepared through enzymatic proteolytic hydrolysis thus digesting collagen proteins into peptides. Collagen or a source thereof is preferably not further added to the composition of the present invention. In a most preferred embodiment, the composition is essentially collagen-free.

The compositions of the present invention may also include one or more amino acids to increase the dermal density. Preferably two or more amino acids are used in combination. Either the L- or D-forms of amino acids are acceptable. Lysine and praline are the most preferred amino acids and are advantageously used in combination. Cysteine, methionine or other amino acids can also be used, if desired. The amino acids may be included in a soluble form such as the hydrochloride, i.e., and L-Lysine hydrochloride. The amino acids are present in an amount of about 2 to 25 weight % each, preferably about 4 to 20 weight % each, and more preferably about 6 to 15 weight % each. A unit dose for each amino acid is typically about 35 mg to 200 mg each, preferably about 50 mg to 150 mg each, and more preferably about 70 mg to 120 mg in the pharmaceutical composition. Additional useful forms of amino acid include the following: a cysteine source, preferably N-acetyl cysteine, can be present in an amount of about 1 to 10 weight %, preferably about 2 to 8 weight %, and more preferably about 3 to 6 weight % of the composition. A methionine source, preferably L-selenomethionine, can be present in an amount of about 0.1 to 5 weight %, preferably 0.2 to 3 weight %, and more preferably 0.3 to 1 weight % of the composition, wherein the selenium component is between about 0.1 to 3 weight % of the methionine source.

One or more transition metal compounds are included in an amount effective to bind collagen and elastic tissue to rebuild the skin. Certain transition metal compounds inhibit the elastase enzyme to inhibit collagen and elastic tissue breakdown. Preferred transition metals include zinc, manganese and copper.

A zinc component can be added to assist in binding collagen and elastic fibers, which both assists in the prevention of wrinkles and the rebuilding of wrinkled skin. Zinc is also known to be an important cofactor for a whole multitude of metalloenzymes, not the least superoxide dismutase, which scavenges the potent oxidizer superoxide.

The zinc component may be any zinc compound or pharmaceutically acceptable salt thereof, preferably zinc gluconate, wherein the zinc is typically present in about 1 to 30 weight % of the composition. The zinc component is present in about 1 to 10 weight %, more preferably about 2 to 7 weight %, and most preferably about 3 to 5 weight % of the composition.

The antioxidants of the compositions of the present invention may be from natural or synthetic sources. In a typical embodiment, the natural source is selected from the group consisting of pine bark, *Vitis vinifera, Camelia sinensis, Aesculus hippocastanum, Gingo biloba, Cardus marianum, Vaccinium myrifilus, Silybum marianum*.

In a suitable embodiment, the one or more natural antioxidants are extractable from grape seed of *Vitis vinifera*.

The natural source of the one or more antioxidants typically contain up to 25% w/w of catechin, epicatechin and gallic acid; up to 90% w/w of epicatechin dimer, trimer and/or tetramer, and/or gallates thereof, and up to 10% w/w of epicatechin pentamer, 5 hexamer and/or heptamer, and/or gallates thereof.

The one or more natural antioxidants may be selected from the group consisting of polyphenols and esters thereof; ascorbic acid (vitamin C) and esters thereof; and pharmaceutically acceptable salts thereof. The polyphenols are typically catechins, leucoanthocyanidins and flavanones; flavanins, isoflavones and anthocyanidins, flavonols, flavonolignans, and oligomers thereof.

Such polyphenols, flavolignans or flavonoids, are antioxidants that occur naturally in many plants. In the present invention isoflavones are extracted from soy, flavones are extracted from borage, thyme or parsley, catechins are extracted from tea (preferably white tea), and proanthocyanidins are extracted from grapes (preferably grape seeds).

In a preferred embodiment, the natural antioxidants is a catechin selected from the group consisting of proanthocyanin A2 and oligomeric procyanidol (OPC), most preferably an oligomeric procyanidol. Flavonolignans are typically silymarin or one of the components thereof such as silybin, silydianin, silychristin and isosilybin.

As stated, a particularly preferred natural antioxidant is an extract from grape seed, i.e. seeds of *Vitis vinifera*, said extract typically being obtained by extracting grape seeds using organic solvents such as acetone and/or ethyl acetate or the like, evaporating the solvents, re-dissolving the residue in water, and filtering and drying the filtrate, e.g. by spray drying or lyolahilisation. In a particularly preferred embodiment, such an extract typically contains up to 25% w/w of catechin, epicatechin and gallic acid; up to 90% w/w of epicatechin dimer, trimer and/or tetramer, and/or gallates thereof; and up to 10% w/w of epicatechin pentamer, hexamer and/or heptamer, and/or gallates thereof.

In addition antioxidants are typically carotenoicis, procarotenoids, 5 tocopherols, phytosterois and ubiquinones. The carotenoids are particularly interesting lipophilic antioxidants and may be selected from the group consisting of a-carotene, 13-carotene, y-carotene, a-carotene, lycopene, zeaxanthin, cryptoxanthine, lutein, and xanthofyll.

A composition of the present invention typically comprises less than 25 weight % beta-carotene, preferably less than 10% beta-carotene, particularly less than 0.1 weight % beta-carotene. Thus, a further aspect of the invention relates to a composition that can achieve the beneficial effects as described infra with very little or essentially no betacarotene.

Tomato extract, comprises lycopene. Preferably, the tomato extract comprises about 5 to 12 weight %, typically approximately 10 weight % lycopene, weight/weight. The tomato extract may be from a single or a blend of tomatoes.

In a typical embodiment, the tomato variety, which is used to prepare the tomato extract, is *Lycopersicum aesculentum*.

In a preferred embodiment of the present invention, the composition comprises 0.1 to 5 weight % of lycopene weight/weight, preferably 0.2 to 4 weight % lycopene, such as 0.3 to 2 weight % lycopene, most preferably 0.3 to 1 weight % lycopene, particularly 0.3 to 0.8 weight %, such as 0.3 to 0.6 weight % lycopene.

In an alternative definition of the composition of the present invention, the composition comprises a plant extract and a cartilage extract wherein the plant extract comprises grape seed extract and lycopene in a weight/weight ratio of about 5:1 to 15:1, preferably about 10:1.

A further suitable composition according to the invention comprises a number of the following ingredients: 10-200 mg, preferably 20-100 mg, more preferably 30-80 mg, even more preferably 35-65 mg, and most preferably 45-55 mg of cartilage extract; 10-200 mg, preferably 20-100 mg, more preferably 30-80 mg, even more preferably 35-65 mg, and most preferably 45-55 mg of plant extracts; 1-50 mg, preferably 3-40 mg, more preferably 5-30 mg, even more preferably 8-25 mg, and most preferably 10-20 mg of vitamin C; 0.1-30 mg, preferably 0.5-20 mg, more preferably 1-15 mg, even more preferably 2-10 mg, and most preferably 3-7 mg of vitamin E; 1-50 mg, preferably 3-40 mg, more preferably 5-30 mg, even more preferably 8-25 mg, and most preferably 10-20 mg of white tea extract; and 1-40 mg, preferably 2-30 mg, more preferably 3-20 mg, even more preferably 5-15 mg, and most preferably 7-12 mg of zinc gluconate, wherein the plant extracts comprise an oligomeric procyanidol and lycopene and the cartilage extract comprises glycosaminoglycans A unit dose for administration may be between 50 and 2000 mg, preferably between 100 and 1500 mg, more preferably between 150 and 900 mg, even more preferably between 200 and 700 mg, and most preferably between 250 and 600 mg.

Although any suitable route of administration may be employed for providing the patient with an effective dosage of the composition according to the present invention, oral administration is preferred. Suitable routes include, for example, oral, rectal, parental, intravenous, topical, transdermal, subcutaneous, intramuscular, and like forms of administration may be employed.

Suitable dosage forms include tablets, troches, dispersions, suspensions, solutions, capsules, patches, suppositories, and the like, although oral dosage forms are preferred. The pharmaceutical compositions used in the methods of the present invention include the active ingredients described above, and may also contain pharmaceutically acceptable carriers, excipients and the like, and optionally, other therapeutic ingredients.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

The compositions for use in the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

Because of their ease of administration, tablets and capsules represent the most advantageous oral dosage unit form, in which case solid pharmaceutical carriers are employed. If desired, tablets may be coated by standard aqueous or nonaqueous techniques.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

Experiment 1: Effect of Antioxidant Composition on Cell Cycle

In a series of experiments the effects of UV on cell cycle distribution in cultured skin fibroblasts was investigated by FAGS analysis. Both UVB (1 kJ/m2) and UVA (250 kJ/m2) were found to cause inhibition of cell cycling. Also for UVA an increase in G1 cells was found one day after irradiation. The effects of antioxidant treatments on the cell cycle of skin fibroblasts were investigated.

Materials and Methods:

Cell culture and irradiation (for further information reference is made to de Leeuw S M, Smit N P, Van Veldhoven M, Pennings E M, Pavel S, Simons J W, Schothorst A A: Melanin content of cultured human melanocytes and UV-induced cytotoxicity. *J. Photochem. Photobiol. B* 2001, 61:106-113):

Fibroblasts from human skin were cultured at 37° C. under 5% carbon dioxide in Dulbecco's Modified Eagle's Medium supplemented with 2.5% fetal calf serum (Hyclone, Logan, Utah) and 100 IU/l penicillin and 100 µg/l streptomycin. For subculturing the cells were detached with 0.25% trypsin/EDTA solution (Gibco) and split 1:5 and maintained in control medium in 90 mm Greiner Petri dishes. After three days the cells were incubated with the different media: control; and vitamin E and C (7 and 10 µM) plus white tea (5 µgram/ml). Three days later the medium was removed and cells were washed with 4 ml PBS and irradiated in the dishes with the lids on in 5 ml Hank's Balanced Salt Solution. A UV source Sellas Sunlight lamp type 2.001 (Sellas, Gevelsberg, Germany) was used for irradiation with a dose of 250 kJ/m2 of UVA. UVASUN blue sheet and UVASUN blue film filter filtered off the wavelengths below 320 nm [2]. The doses were monitored with an IL700A Research Radiometer using a WBS320#801 sensor (International Light Inc., Newburyport, Mass., USA).

Cell cycle distribution by FACS analysis:

After the UVA treatment the cells were maintained overnight in control medium. One hour before harvesting 100 µM BrdU (5-bromo-2-deoxyuridine, Sigma, 85002) was added for incorporation in DNA. Cells were harvested by trypsinization and fixed in 70% ethanol after washing with phosphate buffered saline (PBS).

After removal of excess ethanol cells were incubated for 35 minutes in 0.9 ml 0.1% pepsin in 2M HCl. 1M Tris (2.1 ml) was added and cells were washed 2 times with (PBS-Tween 0.5%). Next the cells were incubated with 100 µl mouse-aBrdU antibodies (DAKO, Bu20A) diluted 1:50 in PBS-Tween with 5% newborn calf serum for 1 hour at room temperature. After washing twice the cells were incubated for 1 hr at 4° C. in the dark with 100 µl goat anti mouse IgG1-FITC (Pharmingen, no 553443) 1:100 in PBS-Tween-NBCS. After washing twice 400 µl of 20 µg/ml propidium iodine, 0.1% ribonuclease (RNase, Sigma) in PBS was added and cells were analyzed by FACS analysis using a FACS-Calibur 1 (Beckton Dickinson). FITC labeling of BrdU was measured in Fl-1 and PI in FL-3 and 10000 events were recorded and analysed by Cell Quest software (Beckton Dickinson).

Results:

FIG. 1 shows distribution of cells in G1 and G2-phase one day after UVA irradiation (dark) compared to sham irradiated fibroblast cultures (grey).

The results conclusively demonstrate differences in percentage of cells found in G1 and G2 phase in VitaminC+Vitamin E+White tea treated cells as compared to control cells. UVA irradiation caused increase of cells present in G1 phase in control cells (G1 arrest). The percentage of cells in G1 phase in VitaminC+Vitamin E+White tea treated cells was considerably lower indicating that less cells were arrested in G1 phase as compared to control cultures. Consequently, the number of cells present in G2-phase in VitaminC+Vitamin E+White tea treated cells was higher compared to the control cells.

Reconstructed Skin Equivalents

Experiment 2: Effect of Composition on Development and Structure of Dermal Extracellular Matrix and Epidermis Using In Vitro Cultured Skin Equivalent The experiments were aimed to examine effect of specific compositions according to the present invention (hereinafter referred to as Composition high and Composition low, or generally Composition) using 3-D in vitro reconstructed skin equivalents (SE).

SE prepared with cells from 19 or 49 year donors were treated with lower and higher concentrations of composition (Composition high and Composition low) or left untreated and cultured for 35, 42 or 60 days. Thereafter the cultures were examined for structure and organization of epidermal and dermal layer. Moreover the synthesis of major extracellular matrix (ECM) components such as fibrillin, elastin, and type I collagen was determined using Q RT-PCR and immunofluorescence.

Materials and Methods:

Cell Cultures

Primary cultures of keratinocytes and fibroblasts were isolated from human kin providing from residus operatoire from plastic surgery. Fibroblasts were grown in Dulbecco's Modified Eagle's Medium (DMEM with Glutamax-1, Life Technologies, Cergy Pontoise, France) supplemented with 10% calf serum (HyClone, Logan, Utah, USA), 20 µg/ml gentamicin (Panpharma, Fougeres, France), 100 IU/ml penicillin (Sarbach, Suresnes, France) and 1 µg/ml amphotericin B (Bristol Myers Squibb, Puteaux, France). For the SE, keratinocytes were grown in a 3:1 mixture of DMEM and Ham's F12 (Life Technologies), respectively, supplemented with 10% calf serum (FCS) (HyClone), 10 ng/ml epidermal growth factor (EGF) (Austral Biologic, San Ramon, Calif., USA), 0.12 IU/ml insulin (Lilly, Saint-Cloud, France), 0.4 µg/ml hydrocortisone (UpJohn, St Quentin en Yvelines, France), 5 µg/ml triiodo-L-thyronine (Sigma, St Quentin Fallavier, France), 24.3 µg/ml adenine (Sigma) and antibiotics. For preparing keratinocyte monolayers, cells, were grown in defined K-SFM medium (Life Technologies) supplemented during 5 days after confluence with 12 mM CaCb.

Skin Equivalent and Dermal Equivalent

Using common art laboratory techniques, 3-D in vitro reconstructed skin equivalents (SE) were prepared in laboratory. The SE both morphologically and biochemically closely resembles native human skin with fully developed dermis, epidermis and stratum corneum (Saintigny G, Bonnard M, Damour 0, Collombel C. Acta. Derm. Venereal, 1993, 73:175-180; Sahuc F, Nakazawa K, Bethod F, Collombel C, Damour O. Wound Rep Reg, 1996, 4:93-102).

The skin equivalent (SE) was prepared as described (Duplan-Perrat et al, 2000). Briefly, Dermal Equivalents (DE) were prepared by adding a suspension of $2 \times 10^5$ fibroblasts/cm$^2$ at top of the collagen-glycosaminoglycanes-chitosan porous sponge Mimedisk® (Coletica, Lyon). All equivalents were cultured for 21 days in fibroblast medium containing 1 mM ascorbic acid 2-phosphate (Sigma). The dermal equivalents (DE) were fed daily. Keratinocytes were seeded On the dermal equivalent at day 14, at a density of 250,000 cells/cm2

After 7 days of submerged culture in the keratinocyte medium, the SE was elevated to the air-liquid interface and cultured in a simplified keratinocyte medium containing DMEM supplemented with 10% calf serum, 10 ng/ml EGF, 0.12 IU/ml insulin, 0.4 µglml hydrocortisone and antibiotics. The medium was supplemented with 50 µg/ml L-ascorbic acid and changed every day. The SE was cultured for in total for 35, 42 or 60 days.

Supplementation with Composition

Tested Composition was added in two concentrations (in order to determine the dose-response relationship) to culture medium at early stage of SE development (from the first change of medium). From the first change of medium following fibroblast seeding on Mimedisk®, Composition was added to the culture medium until the end of the experiment. In parallel, control skin equivalent were prepared with the medium containing only the solvent of active Composition compounds, tetrahydrofurane (THF).

The Composition was added in two concentrations:

|  | Composition with high concentration | Composition with low concentration |
| --- | --- | --- |
| Sodium ascorbate (vitamin C) | 25 µM = 5.0 µg/ml | 12.5 µM |
| Tocopherol acetate (vitamin E) | 17.5 µm = 7.5 µg/ml | 8.8 µM |
| White tea extr. (WT) | 5 µg/ml | 2.5 µg/ml |

-continued

|  | Composition with high concentration | Composition with low concentration |
| --- | --- | --- |
| Grape seed extr (GE) | 5 µg/ml | 2.5 µg/ml |
| Tomato extract (TE) | 10 µg/ml | 5 µg/ml |
| Soy extract (SOY) | 10 µg/ml | 5 µg/ml |
| Cartilage extract | 70 µg/ml | 35 µg/ml |
| Zinc gluconate | 1 µM | 0.5 µM |

Sample Analysis

After 35, 42 or 60 days of culturing, SE were collected and subjected to analysis. Three samples of each SE condition were fixed in formalin and embedded in paraffin. Five µm sections were stained with Hematoxylin-Phloxin-Safran and viewed under light microscope to evaluate dernial and epidermal structure. Further three samples were included in tissue-tek for immunofluorescence measurements and three were frozen at −80° C. for quantitative RT-PCR. lmmunohistology and immunofluorescenceSkin equivalent samples were embedded in OCT Tissue-Tek (Miles, Immunotech, Marseille, France). Six micrometer frozen sections were obtained with Frigocut 2800 cryotome (Reichert-Jung, Paris, France), air dried, blocked in phosphate buffer saline containing 1% (wt/vol) bovine serum albumin. The antibodies used for this study are listed in the following table.

| Antibodies used on skin equivalent | | | |
| --- | --- | --- | --- |
| PRIMARY ANTIGEN | HOST | DILUTION | SOURCE |
| ELASTIN | RABBIT | 1:100 | NOVOTEC (LYON, FRANCE) |
| FIBRILLIN | MOUSE | 1:50 | NEOMARKERS (UNION CITY, CA) |
| FILAGGRIN | MOUSE | 1:100 | BIOMEDICAL TECHNOLOGIES INC. (SOUGHTON, MA) |
| KERATIN 10 | MOUSE | 1:50 | NOVOCASTRA (NEWCASTLE, UK) |
| KI67 | MOUSE | 1:100 | NOVOCASTRA (NEWCASTLE, UK) |
| TYPE I COLLAGEN | RABBIT | 1:1000 | NOVOTEC (LYON, FRANCE) |

The type I collagen antibodies specific for human collagen do not cross react with bovine collagens that were used to prepare the dermal substrate (Noblesse et al, *J Invest Dermatol.*, 2004; 122(3):621-30).

Secondary antibodies, either goat antirabbit IgG (1:50 dilution, Sanofi Diagnostic Pasteur, France) or goat antimouse IgG (1:50 dilution, Cedarlane, Canada) labelled with FITC, were mixed with 0.1% Evans Blue to reduce nonspecific staining of the sponge network (Kieny and Mauger, 1984). For controls, the primary antibody was omitted. Multiple sections of each specimen were processed to ensure representative samples.

Quantitative RT-PCR

To follow the production of mRNA for elastin, fibrillin 1 and type I collagen at day 42 and 60, we used quantitative RT-PCR. The total RNA of the skin equivalents were extracted using the "SV 96Total RNA Isolation System" from Promega. For each sample, 100p1 of purified total RNA were obtained, quantified at 260 nm with a spectrophotometer (spectramax190; Molecular Devices) and kept frozen at −80° C. until use.

For the quantitative RT-PCR, we designed primers specific for each gene. We performed the one-step quantitative RT-PCR with the specifics primers, using the "QuantiTect SYBR Green RT-PCR" kit (Qiagen). The reaction mix contained: the SYBR Green buffer 1×; the two specific primers at 0.5 µM; 1 µl of enzyme mix; 50 ng of total sample RNA; qsp 50p1 with RNase-free water. The reaction was run in the OPTICON® thermocycler (MJ Research). After the run, the samples were run on a 2% agarose gel to ensure that the PCR products were pure.

Figure 2:
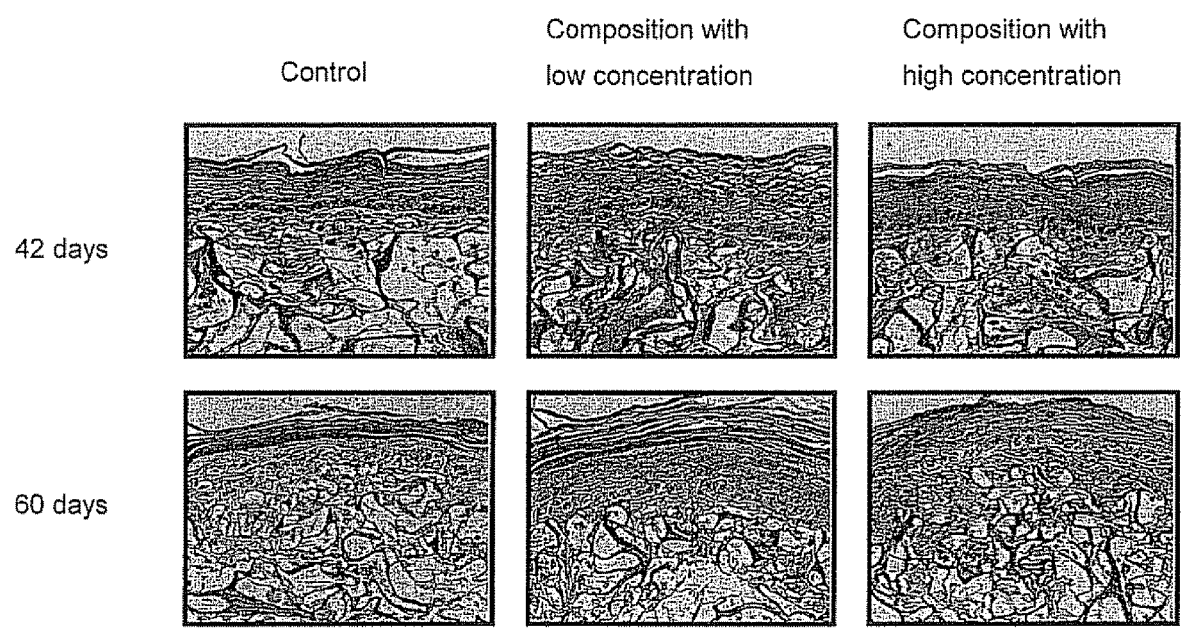
FIG. 2 illustrates the effect of a composition with high and low concentration on skin equivalent reconstructed from dermal fibroblasts of a 19 year old donor.

Results:

Effect of Composition on Skin Equivalent Reconstructed from Dermal Fibroblasts from 19 Year Old Donor Regardless of concentration, Combination delayed epidermal senescence. FIG. 2 shows the effect of Composition with high and low concentration on skin equivalent reconstructed from dermal fibroblasts from 19 year old donor. Hematoxylin-Phloxin-Safran staining. Magnification 25×.

At 42 days of culture, epidermis in control samples showed typical structure with several layers of viable epidermal cells and stratum corneum (FIG. 2, Control, 42 days). With prolonged culture time (Control, 60 days), the epidermis become rather thin, completely differentiated and showed some features typical for deterioration of SE kept in culture for long time (epidermal senescence). Treatment with Combination resulted in delay of the senescence as demonstrated by formation of thick, pluristratified and renewing epidermis. (FIG. 2, Composition high and low, 60 days). Effect on dermis was not evident.

Effect of Composition on skin equivalent reconstructed from dermal fibroblasts from 49 year old donor.

Figure 3:
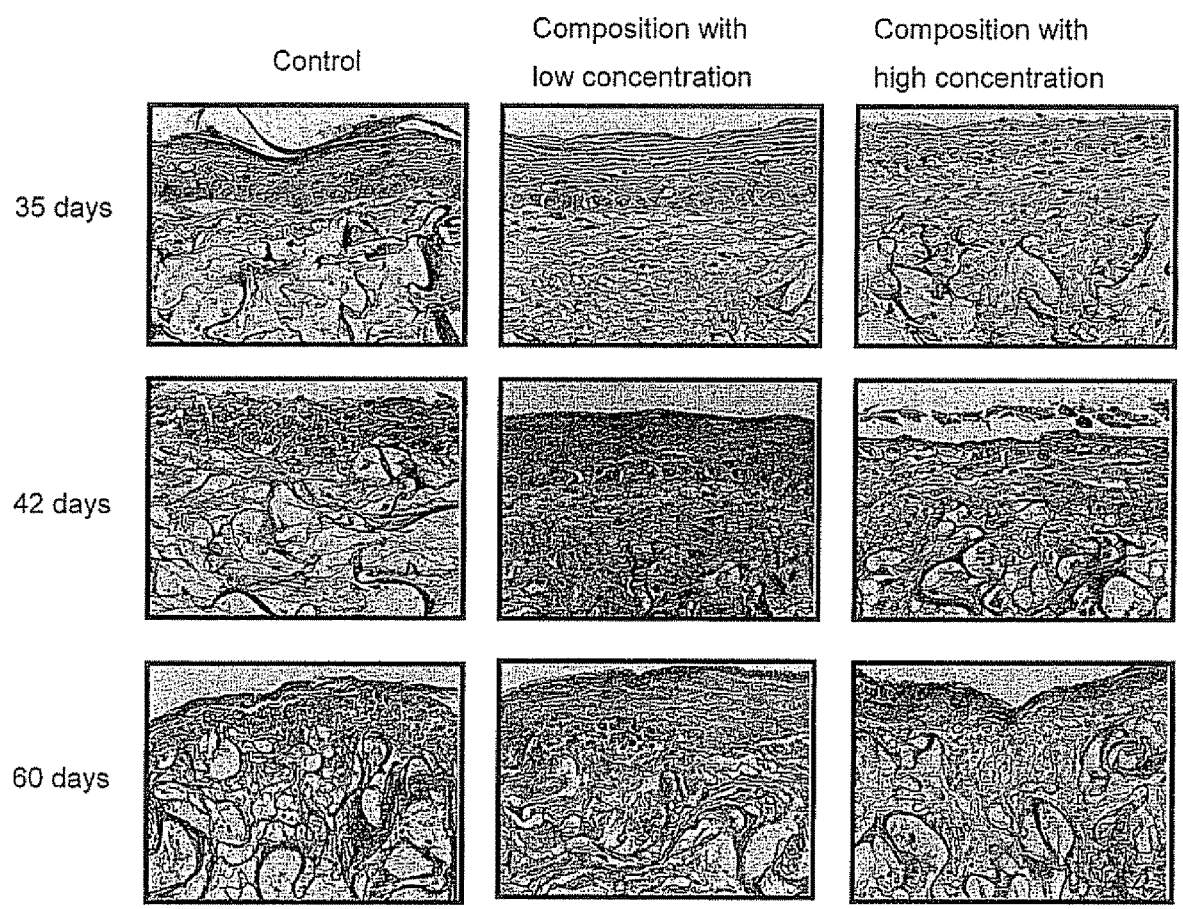
FIG. 3 illustrates the effect of the composition with high and low concentration on skin equivalent reconstructed from dermal fibroblasts of a 49 year old donor.

FIG. 3 shows the effect of Composition with high and low concentration on skin equivalent reconstructed from dermal fibroblasts of 49 year old donors. Hematoxylin-Phloxin-Safran staining. Magnification 40×.

Combination delayed epidermal senescence, stimulated formation of dense dermal structure and delayed dermal senescence in SE from 49 year old donors. Combination with low concentration showed superior effects (FIG. 3).

There were evident differences between control SE prepared with fibroblasts from 19 year old and 49 year old donors. Control samples from 49 year old donors showed faster deterioration of both epidermal and dermal structures during culture time than control samples from 19 year old cells (compare Control at day 42 and 60 on FIGS. 2 and 3). At both day 42 and 60, the Control samples of SE from 49 year old cells looked even more deteriorated and differentiated showing a residue of cornified epidermis as compared to the respective Controls of SE 19. This effect was reduced by treatment with Combination. Combination with lower concentration gave more positive results as compared to Combination with higher concentration. The resulting SE was well developed with dense dermis and thick, well stratified epidermis. Compare Control and Combination with lower concentration at day 60 on FIG. 3.

Results proved conclusively that treatment of skin equivalents with Combination had positive effect on structure, quality and maintenance of both epidermis and dermis. Combination delayed epidermal senescence by stimulating growth of epidermal keratinocytes which led to thick, well structured and renewing epidermis regardless the age of cell donor. There was also marked effect on formation of dense dermal structure and delayed senescence of dermis in SE from 49 year old donors.

Hence, Composition treatment, i.e. treatment with the compositions according to the present invention, had a very positive effect on epidermis: it reduced epidermal senescence and stimulated keratinocytes growth and renewal regardless the age of the cells even though the effect was more pronounced on SE from old cells. Compared to untreated samples that showed decrease of epidermal thickness and no cell renewal after 42 days in culture, Composition treatment resulted in maintenance of thick renewing epidermis. In dermis, Composition stimulated production and deposition of ECM (extracellular matrix) components.

Immunohistochemistry and Quantitative RT-PCR

For the SE prepared with Composition (low as well as high concentration) treated fibroblasts from the 49 years old donors showed a significant increase of mRNA type I-collagen, fibrillin and elastin synthesis after 60 days of culturing. Such effects were not observed for fibroblasts from 19 years old donors. This effect was confirmed by immunohistochemical staining of collagen type I, elastin and fibrillin proteins. Furthermore the number of cells expressing the proliferation marker Ki67 after 60 days was 4 times higher in Composition treated fibroblasts relative to the control; this applied to fibroblasts from both 19 years and 49 years old donors.

Experiment 3: In Vivo Experiments

Tablets were prepared according to the following lists of ingredients by conventional procedures:

| | |
|---|---|
| Sodium ascorbate | Sodium ascorbate |
| d-a-tocopheryl acetate | d-a-tocopheryl acetate |
| White tea extract | White tea extract |
| Soy extract | Soy extract |
| Cartilage extract | Cartilage extract |
| Grape seed extract | Chamomile extract |
| Tomato extract | Grape seed extract |
| Zinc gluconate | Tomato extract |
| Pharmaceutically acceptable excipients | Zinc gluconate |
| | Pharmaceutically acceptable excipients |

Tablet II

Testing of the Product:

The tablets (TABLET I in the morning and TABLET II in the evening) were administered to test 50 female subjects to determine the effects on the dermal density, firmness, and presence of fine lines and wrinkles of the skin. The trial was completed after 6 months. Test subjects not in the control group, who consumed placebo tablets, consumed two (2) tablets of the test material of Tablet 1 and two (2) tablets of the test material of Tablet 2 daily with meals. A total of 38 subjects completed the study with active tablets and 43 with placebo tablets.

The following inclusion criteria applied: (i) 45-65 years (one to five years post menopausal—70% of the subjects used no HRT and 30% of the subjects used HRT minimum 3 months before study start), (ii) Skin types I-III (Fitzpatrick; Fitzpatrick 11-111 and Glogau 11-111 enrolled), (iii) Moderate to advanced signs of ageing (Glogau 11-111), (iv) Photodamage on the back of the hands.

Results Clinical Grading:

The investigator examined subjects at specific locations on the right or left side of the face, the back of the right or left hand and on the décolletage (chest) for the following skin aging parameters:

Face
  Fine Wrinkles (periocular area)
  Tactile Roughness/Dryness
  Fine Wrinkles (perioral area/lip lines)
  Mottled Hyperpigmentation
  Laxity (assessed by vertical lifting of skin with fingers)
  Sagging (visual dropping of skin around the mouth area)
  Under Eye Dark Circles
  Telangiectasia
  Overall Facial Appearance
Hand:
  Crepyness
  Thinness
  Mottled Hyperpigmentation
Decolletage:
  Crepyness
  Mottled Hyperpigmentation
  Overall Appearance Results of the clinical grading were recorded using the following scale:

0<3 Mild

3<6 Moderate

6<9 Severe

Comparison between the active tablet and placebo was performed. The parameters indicated with an asterisk indicate where the active tablet performed significantly better than placebo (p<0.05). A decrease in value (arbitrary units) indicates improvement.

Results Clinical Grading

| Clinical grading change from baseline to month 6 | Active tablet (n = 38) | Placebo (n = 43) |
|---|---|---|
| Face, forehead wrinkles | −0.387* | −0.167 |
| Face, periocular wrinkles | −0.761* | 0.477 |
| Face, perioral wrinkles | −0.626* | −0.298 |
| Face, mottled pigmentation | −0.718* | −0.33 |
| Face, tactile laxity | −0.961* | −0.551 |
| Face, sagging visual | −0.618* | −0.302 |
| Face, under eye dark circles | −0.447* | −0.179 |
| Face, overall | −0.813* | −0.377 |
| Hands, crepyness | −0.908* | −0.519 |
| Décolletage, overall appearance | −0.421* | −0.67 |

Ultrasound Skin Density:

Ultrasound has been used for over 20 years in clinical and practical medicine. It is a reliable, non-invasive means of measuring dermal density. The ultrasound waves are reflected by the skin's structural elements, which are shown as coloured spots on the ultrasound picture. The more coloured spots, the denser the skin structure.

A DUBplus (Taberna, Pro Medicum, AG) Ultrasound unit was used to take a B-scan image of the right or left crow's foot area (chosen by the grader). The DUBplus Ultrasound unit having a standard 20 MHz transducer was used with a focal distance of 12 mm and 40 dB resolution. A gain setting of 28 db produced the best overall visualization of the full skin thickness at the test sites. The measurements were taken with the probe oriented perpendicular to the body axis in the crow's foot area. Alternatively the measurement may be performed near the glabellar area of the forehead. Increased density values suggest a thickening of the epidermal and dermal tissue and can be used as an indication for improved dermal structure. A significant improvement (p<0.05) in dermal density after 6-month use was found in the active tablet supplemented group compared to the placebo group.

Overview of Results:

| Statistical significance after 6 months (p < 0.05) |
| --- |
| Clinical grading, Face |
| Active tablets vs. placebo |
| |
| Forehead wrinkles p = 0.01 |
| Periocular wrinkles p = 0.046 |
| Perioral wrinkles p = 0.01 |
| Mottled pigmentation p = 0.002 |
| Laxity (tactile) p = 0.007 |
| Sagging (visual) p = 0.008 |
| Under eye dark circles p = 0.01 |
| Overall appearance p = 0.0001 |
| Clinical grading, Body |
| Active tablets vs. placebo |
| |
| Décolletage overall p = 0.0003 |
| Hand crepyness p = 0.004 |
| Skin density, ultrasound scanning |
| Active tablets vs. placebo |
| |
| skin density, p = 0.0001 |

The invention claimed is:

1. An orally administered tablet or capsule for the treatment of cutaneous signs of aging in a mammal comprising an effective amount of Vitamin E, vitamin C, white tea extract, and an extract comprising glycosaminoglycans.

2. The tablet or capsule of claim 1 further comprising: Naturally occurring antioxidants extracted from grape seed, tomato, soy and/or chamomile, and at least one transition metal component.

3. The tablet or capsule of claim 2, wherein the extract comprising glycosaminoglycans is cartilage extract.

4. The tablet or capsule of claim 3, wherein the cartilage extract comprises chondroitin sulphate, keratan sulphate, hyaluronic acid, or dermatan sulphate or mixtures thereof.

5. The tablet or capsule of claim 2, wherein the transition metal component is zinc.

6. The tablet or capsule of claim 5, wherein zinc is in form of zinc gluconate.

7. The tablet or capsule of claim 6 further comprising pharmaceutically acceptable excipients.

8. A composition in the form of a tablet or capsule comprising: 0.1 to 60 weight % of vitamin E, 0.2 to 90 weight % of vitamin CU, and 0.2 to 90 weight % of white tea extract based on the total weight of the composition.

9. The composition in the form of a tablet or capsule of claim 8 further comprising 5 to 95 weight % of naturally occurring antioxidants extracted from grape seed, tomato, and/or chamomile, based on the total weight of the composition.

10. The composition in the form of a tablet or capsule of claim 9 further comprising 5 to 95 weight % of soy extract based on the total weight of the composition.

11. The composition in the form of a tablet or capsule of claim 10, wherein vitamin E constitutes 0.5 to 20 weight % of the total weight of the composition.

12. The composition in the form of a tablet or capsule of claim 11, wherein vitamin C constitutes 1 to 30 weight % of the total weight of the composition.

13. The composition in the form of a tablet or capsule of claim 12, wherein vitamin E constitutes 1 to 10 weight % of the total weight of the composition.

14. The composition in the form of a tablet or capsule of claim 13, wherein vitamin C constitutes 1 to 15 weight % of the total weight of the composition.

15. A tablet or capsule comprising the pharmaceutical composition of claim 8 along with pharmaceutically acceptable excipients.

16. A tablet or capsule formulation comprising an effective amount of Vitamin C, Vitamin E, White tea extract, Soy extract, Cartilage extract, Grape seed extract, Tomato extract, Zinc gluconate, and Pharmaceutically acceptable excipients.

17. The tablet or capsule formulation of claim 16 further comprising chamomile extract.

* * * * *